United States Patent [19]

Ariura et al.

[11] Patent Number: 4,474,570
[45] Date of Patent: Oct. 2, 1984

[54] IONTOPHORESIS DEVICE

[75] Inventors: Shunsuke Ariura, Matsudo; Tadashi Ogata, Fuchu; Norie Kashima, Tokyo; Michiyo Morihata, Fuchu, all of Japan

[73] Assignee: Kabushikikaisya Advance Kaihatsu Kenkyujo, Tokyo, Japan

[21] Appl. No.: 396,460

[22] Filed: Jul. 8, 1982

[30] Foreign Application Priority Data

Jul. 10, 1981 [JP] Japan ............................ 56-106935

[51] Int. Cl.³ ............................................. A61N 1/30
[52] U.S. Cl. ....................................... 604/20; 128/798
[58] Field of Search ............... 604/20; 128/640, 641, 128/639, 802, 419 R, 803, 798

[56] References Cited

U.S. PATENT DOCUMENTS

| | | | |
|---|---|---|---|
| 4,274,420 | 6/1981 | Hymes | 128/641 |
| 4,299,231 | 11/1981 | Karmann et al. | 128/639 |
| 4,317,457 | 3/1982 | Guillot | 128/802 |
| 4,383,529 | 5/1983 | Webster | 128/802 X |
| 4,398,545 | 8/1983 | Wilson | 128/803 X |
| 4,406,658 | 9/1983 | Lattin et al. | 128/419 R |
| 4,416,274 | 11/1983 | Jacobsen et al. | 604/20 |

FOREIGN PATENT DOCUMENTS 1965195  7/1971  Fed. Rep. of Germany ...... 128/640

Primary Examiner—Lee S. Cohen
Attorney, Agent, or Firm—Finnegan, Henderson, Farabow, Garrett & Dunner

[57] ABSTRACT

An iontophoresis device having lightweight and being capable of very easy, direct application to the skin is disclosed. This iontophoresis device comprises: (a) a first conductive electrode consisting essentially of a conductive gel layer containing or capable of containing an ionic agent and a current-distribution conductive member layer, the two layers being integrally laminated together; (b) a second conductive electrode consisting essentially of a conductive gel layer and a current-distribution conductive member layer, the two layers being integrally laminated together; and (C) a lightweight battery. The first and second electrodes are electrically connected to the lightweight battery so that a closed circuit is formed when the above members are applied to the skin.

12 Claims, 6 Drawing Figures

IONTOPHORESIS DEVICE

The present invention relates to an iontophoresis device for epidermal application, more specifically to an iontophoresis device having a light weight and capable of directly and very easily being applied to the human skin.

Recently, iontophoresis has come into increasing attention as an effective method for topical application of ionic agents or drugs by promoting absorption through the skin. Iontophoresis techniques are disclosed in, for example, Glass, J. M. et al., Int. J. Dermatol. 19,519 (1980); Russo J., Am. J. Hosp. Pharm. 37,843 (1980); Gangarosa, L. P. et al., J. Pharmacol. Exp. Ther. 212,377 (1980); Kwon, B. S. et al., J. Infect. Dis 140,1014 (1979); Hill, J. M. et al., Ann. N.Y. Acad. Sci. 284,604 (1977) and Tannebaum, M. Phys. Ther. 60,792 (1980).

The iontophoresis disclosed in these prior arts is usually carried out by connecting the output terminal of a continuous direct current generator or pulsed direct current generator to a first or active electrode composed of a metal plate or other conductive substances covered with a moistened pad of porous material impregnated with an aqueous solution of ionic drug and a second or indifferent electrode structured similar to the first electrode but not soaked with the drug. From the above, it is clear that actual application of iontophoresis is very troublesome. While iontophoresis is a very effective method for drug application, this troublesome application had limited its spread. Further, the first and second electrodes have usually been fixed to the affected area of the body by means of, for example, rubber band, and the electric current flows through the skin. This has made it easy for burns to occur due to poor contact between the skin and the electrodes. Thus, an ammeter must be continually monitored during the application. For these reasons, conventional iontophoresis cannot become popularized as a home curative means, although it can be used in hospitals and clinics.

An object of the present invention is to eliminate the above-mentioned problems in the prior arts by providing an iontophoresis device having a light weight and capable of directly and very easily being applied to the patient's skin with a simple operation and even for a long time.

Other objects and advantages of the present invention will be apparent from the description set forth hereinbelow.

In accordance with the present invention, there is provided an iontophoresis device comprising:

(a) a first conductive electrode consisting essentially of a conductive gel layer containing or capable of containing an ionic agent and a current-distribution conductive member layer, the two layers being integrally laminated together;

(b) a second conductive electrode consisting essentially of a conductive gel layer and a current-distribution conductive member layer, the two layers being integrally laminated together; and (c) a lightweight battery, said first and second electrodes being electrically connected to said lightweight battery so that a closed circuit is formed when the above members are applied to the patient's skin.

The present invention now will be illustrated in detail with reference to the accompanying drawings, wherein.

Figure 1:
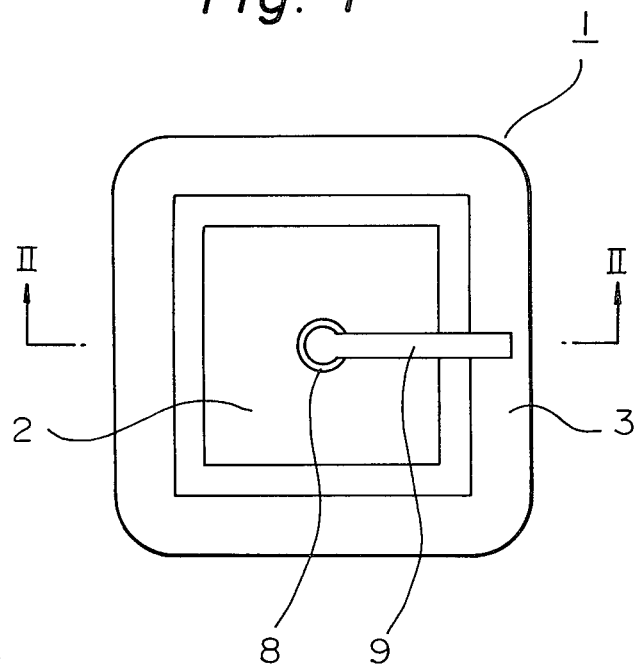
FIG. 1 is a plan view illustrating a first embodiment of the present iontophoresis device.
Figure 2:
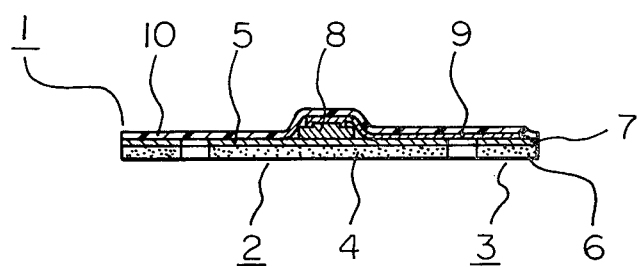
FIG. 2 is a cross-sectional view of the first embodiment of the present iontophoresis device, taken along the line II—II of FIG. 1.
Figure 3:
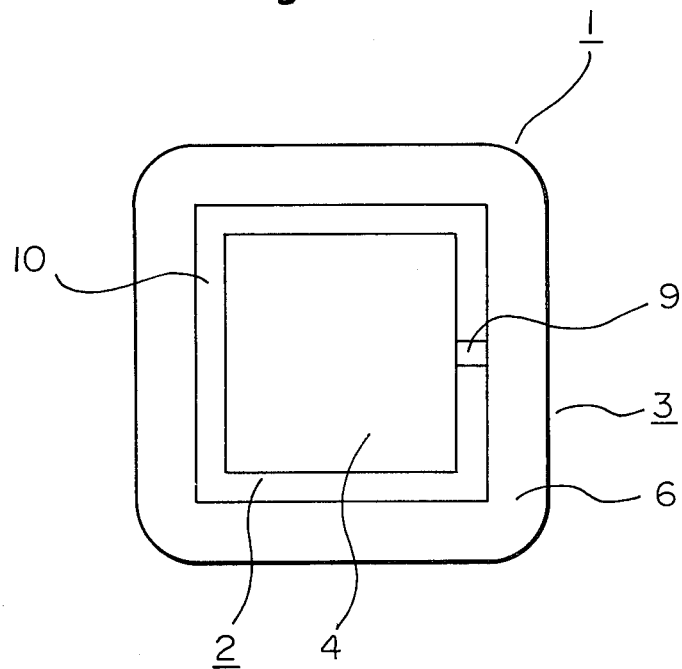
FIG. 3 is a bottom plan view of the first embodiment of the present iontophoresis device.

Referring to FIGS. 1 to 3, illustrating a first embodiment of the present iontophoresis device, iontophoresis device 1 comprises first electrode 2, second electrode 3, and button battery 8. First electrode 2 is composed of conductive gel layer 4, in the form of a flexible sheet or film containing or capable of containing an ionic agent and of current-distribution conductive member layer 5, which layer 5 is formed by aluminum foil or another metallic foil a conductive rubber or resin film. Gel layer 4 and current distribution conductive member layer 5 are integrally laminated together.

Second electrode 3 is composed of conductive gel layer 6 formed as a flexible sheet or film and of current-distribution conductive member layer 7, which layer 7 is formed by a metallic foil or a conductive rubber or resin film. Gel layer 6 and current distribution conductive member layer 7 are integrally laminated together.

Button battery 8 is arranged near the central portion of the top surface of first electrode 2 in such a manner that one of the poles of battery 8, for example, negative pole (−), contacts current-distribution conductive member layer 5 of first electrode 2. The positive pole (+) of battery 8 is connected to current-distribution conductive member layer 7 of second electrode 3 by means of lead wire 9 made of, for example, aluminum foil. The bottom surface of lead wire 9, other than the both end portions thereof, is provided with an insulating coating.

Iontophoresis device 1 is also provided with insulating backing layer 10. Insulating backing layer 10 is composed of, for example, a flexible sheet or film made of a nonconductive synthetic resin. First and second electrodes 2 and 3 are fixed on insulating backing layer 10 in such a manner that first electrode 2 is separated from second electrode 3. First and second electrodes 2 and 3 and battery 8 are integrally connected together by means of insulating backing layer 10.

Iontophoresis device 1 is applied to the human body by placing first electrode 2, containing the desired ionic agent or drug, in conductive gel layer 4, in contact with the intended portion of the patient's body. Thus, electrodes 2 and 3 form a closed circuit through the human body, thereby promoting the penetration or absorption of the ionic agent or drug contained in conductive gel layer 4 of first electrode 2 through the skin.

Figure 4:
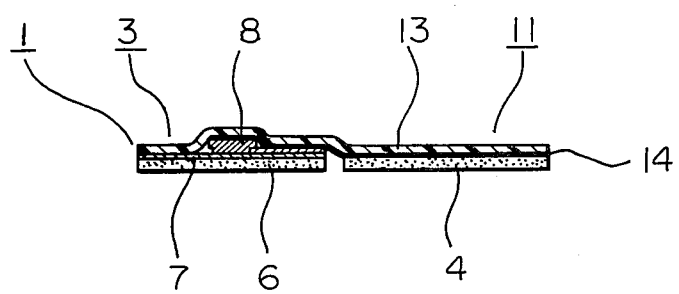
FIG. 4 is a cross-sectional view of a second embodiment of the present iontophoresis device.

Referring to FIG. 4, in a second embodiment of the present iontophoresis device, iontophoresis device 1 comprises first electrode 11, second electrode 3, and button battery 8. First electrode 11 is composed of conductive gel layer 4 containing or capable of containing an ionic agent or drug and of current-distribution conductive member layer 14. Gel layer 4 and current-distribution conductive member layer 14 are integrally laminated together. Current distribution conductive member layer 14 of this embodiment is formed by vapor deposition of aluminum on a portion of insulating backing 13 composed of a flexible nonconductive sheet or film made of, for example, polyvinylidene chloride. Button battery 8 is arranged on the upper surface of current-distribution conductive member layer 7 of second electrode 3 in such a manner that the positive pole of second electrode 3 directly contacts the upper surface of current-distribution conductive member layer 7. On the other hand, current-distribution conductive member layer 14 of first electrode 11 is connected with the negative pole of button battery 8. Second electrode 3 is fixed on the portion of insulating backing 13 where current-distribution conductive member layer 14 is not formed. Thus, first electrode 11, second electrode 3, and button battery 8 are integrally connected together and supported by insulating backing 13.

The second embodiment of the present iontophoresis device enables a flexible, very thin iontophoresis device since the first electrode is composed of a laminate substantially containing two layers.

Figure 5:
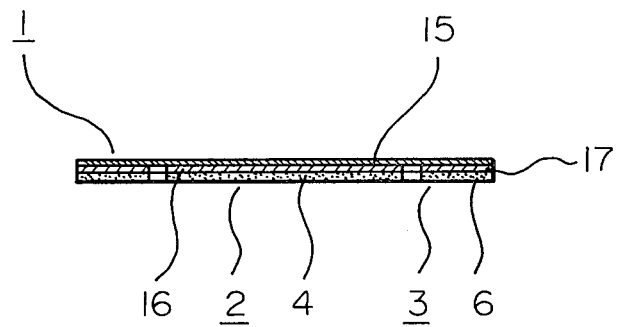
FIG. 5 is a cross-sectional view of a third embodiment of the present iontophoresis device.

Referring to FIG. 5, in a third embodiment of the present iontophoresis device, iontophoresis device 1 comprises first electrode 2, second electrode 3, and sheet battery 15 as the lightweight battery. Current-distribution conductive member layers 16 and 17 composed of, for example, copper foil or a carbon fiber nonwoven fabric are placed on one surface of sheet battery 15. Conductive gel layer 4 containing an ionic agent or drug is laminated on the one of the poles of sheet battery 15 and conductive gel layer 6 not containing ionic agent or drug is laminated on the another pole.

The third embodiment of the present iontophoresis device enables a very thin, flexible and flat iontophoresis device since the sheet battery is very thin (i.e., about 0.5 to 2 mm). The output terminal of the sheet battery may be formed as a flat face. This output terminal also functions as the current-distribution conductive member layer.

Figure 6:
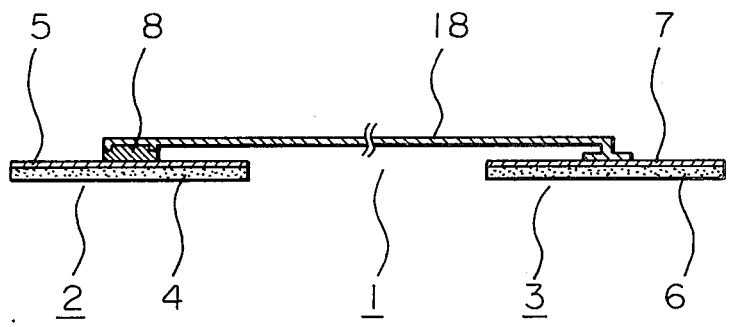
FIG. 6 is a cross-sectional view of a fourth embodiment of the present iontophoresis device.

Referring to FIG. 6, in a fourth embodiment of the present iontophoresis device, iontophoresis device 1 comprises first electrode 2, second electrode 3, and button battery 8. The one pole of button battery 8 is connected to current-distribution conductive member layer 5. The another pole of button battery 8 is connected, through lead wire 18, to current-distribution conductive member layer 7 of second electrode 3.

The fourth embodiment of the present iontophoresis device enables the first electrode to be applied to the body apart from the second electrode by any distance, limited only by the length of the lead wire. Thus, the iontophoresis device can be easily applied to the intended portion of patient even when the portion is very small or has a relatively large curvature radius. Furthermore, when a large amount of perspiration comes out on the skin, especially at a high temperature and high humidity, the iontophoresis device is not affected by the electric current flowing on the surface of the skin during application since the two electrodes are separately placed.

The constituents of the iontophoresis device of the present invention will now be explained in detail hereinbelow.

Conductive gel layers

The conductive gel layers of the first and second electrodes of the present iontophoresis device are composed of various hydrophilic natural or synthetic resins: for example, natural resinous polysaccharides such as karaya gum, tragacanth gum, and Xanthan gum; vinyl resins such as partially saponified polyvinyl alcohol, polyvinyl formal, polyvinyl methyl ether and copolymers thereof, polyvinyl pyrrolidone, and polyvinyl methacrylate; and acrylic resins such as polyacrylic acid and sodium salts thereof, polyacryl amide and partially hydrolyzed products thereof, partially saponified products of polycrylic acid esters, and copoly (acrylic acid-arylamide). These hydrophilic natural or synthetic resins are softened and plasticized with water and/or polyols such as ethylene glycol, propylene glycol and glycerine and are molded to the form of a flexible sheet or film. The resultant gel layer has a shape retention property and adhesiveness to the skin.

An ionic agent or drug is further included, or is to be included just before application to the skin, in the conductive gel layer of the first electrode, whereby the conductivity of the gel layer increases. If desired, a supporting electrolyte is optionally added to the gel layer as in the case of the so-called electrophoresis gel.

If desired or necessary, various electrolytes, such as sodium chloride, sodium carbonate, and potassium citrate, can be added to the conductive gel layer of the second electrode to provide a sufficient conductivity. The electrolyte is usually added in an amount of about 1% to 15% by weight, based on the total weight of the gel layer.

The resultant conductive gel layers suitable for use in the present invention are in the form of a flexible sheet or film and can closely adhere to the skin. Therefore, the skin contact resistance is low. As a result, the ionic agent or drug effectively penetrates into the skin. Furthermore, it is advantageous from the viewpoint of practical application that the iontophoresis device can be directly applied to the intended skin without using any adhesive means such as a pressure-sensitive adhesive tape.

If the gel layer of the second electrode is composed of an adhesive gel as mentioned above and the gel layer of the central active electrode, as shown in FIG. 1, is composed of nonadhesive hydrogel, such as agar gel, as mentioned hereinbelow, the above-mentioned advantages can also be obtained.

Especially when the above-mentioned natural resinous polysaccharides such as karaya gum are used as the basic material of the gel layers, gel layers having not only electrochemically good conductivity but also desirable skin compatibility or adaptability can be obtained. This is due to the pH buffer action (pH 4-5) or skin protecting property based on the natural high polymer acid structure, remarkably high water-retention characteristics, and moderate skin adhesiveness thereof.

When karaya gum is used as the above-mentioned polysaccharide, the gel composition selected is usually 20 to 70 parts by weight of karaya gum and 80 to 30 parts by weight of a polyol, such as glycerine or propylene glycol (containing 0% to 50% by weight of $H_2O$ based on the weight of the polyol), depending upon its intended use. Since the resultant gel has sufficient water-retention characteristics, an ionic agent or drug in the form of aqueous solution can added to the gel layer before usage. The addition of electrolytes to the second electrode is not necessarily required since gel composed of karaya gum has sufficient conductivity by itself.

When the gel layers are compounded or prepared, the same electrochemical considerations should be given as with the preparation of the so-called electrophoresis gel. Generally, the gel layer is prepared so as to provide the desired ion mobility or conductivity, depending upon the kind of the ionic agent or drug, the administered amount (dose required), the application period, the output power of the battery, the contact area to the skin, and other factors.

Examples of the preparation and composition of the conductive gel layers suitable for use in the present iontophoresis device are given below. The examples are given in reference to the conductive gel layers for the second electrodes, however, the conductive gel layers of the first electrodes can be prepared in the same manner except that all or part of the electrolytes such as sodium chloride is replaced with the desired ionic agent or drug. The desired ionic agent or drug can be incorporated into the gel layer at the time when the gel layer is prepared or just before the iontophoresis device is actually applied to the skin.

1. Thirty grams of powdered polyvinyl alcohol having a weight-average molecular weight of 440,000 and a saponification value of about 60% was prepared in a conventional manner. Forty grams of a 10% NaCl solution in distilled water, preheated to a temperature of 80° C., and 30 g of glycerine were added to the powdered polyvinyl alcohol. The mixture was thoroughly stirred. The resultant mixture was hot-pressed for about 20 minutes at a pressure of 0.6 kg/cm$^2$G in a hot press heated to a temperature of 80° C. Thus, a flexible sheet having a thickness of 3 mm was obtained. The flexible sheet thus obtained had a sufficient adhesiveness to the skin and a specific resistance of 0.8 kΩ·cm.

2. Electrically conductive gel layers in the form of a flexible sheet having the following compositions were prepared in the same manner as described above.

EXAMPLE A

| | |
|---|---|
| Polyvinyl pyrrolidone (a weight-average molecular weight of 360,000; PVP-K90 manufactured by GAF Corporation) | 20 g |
| 10% NaCl solution in distilled water | 40 g |
| Glycerine | 40 g |

The resultant sheet had a sufficient adhesiveness to the skin and a specific resistance of 0.2 kΩ·cm.

EXAMPLE B

| | |
|---|---|
| Polyvinyl formal (a weight-average molecular weight of 1,600,000, a formalization degree of 15%, and a saponification degree of the starting polyvinyl alcohol of 60%) | 15 g |
| 5% NaCl solution in distilled water | 70 g |
| Propylene glycol | 15 g |

The resultant sheet had a sufficient adhesiveness to the skin and a specific resistance of 1.0 kΩ·cm.

EXAMPLE C

| | |
|---|---|
| Polyvinyl acetoacetal (a weight-average molecular weight of 440,000, an acetalization degree of 30%, and a saponification degree of the starting polyvinyl alcohol of 70%) | 40 g |
| 15% NaCl solution in distilled water | 50 g |
| Ethylene glycol | 10 g |

The resultant sheet had a sufficient adhesiveness to the skin and a specific resistance of 0.75 kΩ·cm.

3. Forty grams of sodium polyacrylate having a weight-average molecular weight of 12,000,000 to 13,000,000 (Acoflock A-130 manufactured by Mitsui Cyanamide Co.) was uniformly mixed with 30 g of a 10% NaCl solution in distilled water and 60 g of glycerine. The resultant mixture was heated under pressure at a temperature of 80° C. for 10 minutes to provide a flexible sheet. The sheet thus prepared had a moderate adhesiveness to skin and a specific resistance of 0.5 kΩ·cm after allowing to stand for 1 day.

4. Thirty grams of polyacryl amide having a weight-average molecular weight of 13,000,000 to 15,000,000 (Acoflock N-100 manufactured by Mitsui Cyanamide Co.) was uniformly mixed with 50 g of a 10% NaCl solution in distilled water and 20 g of glycerine and then hot pressed to form a sheet in the same manner as mentioned above. The specific resistance of the resultant sheet was 0.9 kΩ·cm.

5. Thirty grams of karaya gum was uniformly mixed with 30 g of 5% NaCl solution in distilled water and 40 g of glycerine and then hot-pressed to form a sheet in the same manner as mentioned above. The specific resistance of the resultant sheet was 0.65 kΩ·cm.

In addition to the above-exemplified hydrophilic polymeric substances, various known hydrophilic polymeric substances usable as so-called bioelectrode materials can also be used. Such materials are disclosed in, for example, Japanese patent application Laid-Open (Kokai) Nos. 52-95895, 54-77489, 55-52742, 56-15728, 56-36939, and 56-36940; Japanese patent publication (Kokoku) Nos. 48-28747, 50-27317, and 52-9946; U.S. Pat. Nos. 3,490,440, 3,640,741, 3,665,064, 3,989,050, 3,998,215, 4,016,869, 4,066,078, and 4,125,110; British Pat. No. 1,557,254; and Japanese patent application Nos. 56-14936 and 56-46531. Typical examples of such materials are polyethylene glycol, carboxy polymethylene, methyl cellulose, sodium alginate and polyethylene oxides.

Thus, any hydrophilic polymeric substances which can be softened and plasticized with water and/or polyols to form viscoelastic gels, desirably having adhesiveness to the skin, can be used as the basic gel material of the conductive gel layers of the present iontophoresis device. These substances are generally selected taking into consideration the compatibility thereof with the ionic agent or drug to be used, the compatability with the skin, and the electrical conductivity. These gel layers can be disposed or reused.

As is clear from the above examples, wide varieties of hydrophilic polymeric substances can be used, in the formation of conductive gel layers suitable for use in the present invention, by softening and plasticizing said substances with water and/or alcohols. There are no limitations on the special basic materials or the special composition thereof. Generally speaking, the gel composition is selected from those containing 10% to 70% by weight of hydrophilic polymeric substances and the remainder of water and/or polyols in order to obtain the desired shape retentiveness.

Although the above-mentioned conductive gel layers have a sufficient adhesiveness to the skin by themselves, additional pressure-sensitive adhesive components such as acrylic type adhesives, and vinyl acetate emulsion type adhesives can be incorporated into the gel layers, if desired. On the other hand, when nonadhesive hydrogels such as agar gels are used, skin adhesive means such as pressure-sensitive adhesive tapes should be arranged on, for example, the outer circumferential portion of the present iontophoresis device, as shown in FIG. 1.

Ionic Agent or Drug

Various kinds of agents or drugs can be used in the present iontophoresis device so long as they can dissociate into ions in water or polyols. Examples of ionic agents or drugs usable in the present invention are potassium iodide, procaine hydrochloride, methacholine, various skin vitamins such as vitamins $B_1$, $B_2$, $B_6$, and C, histamine, sodium salicylate, dexamethasone, epinephrine, hydrocortisone, idoxuridine, and undecylenic acid salts.

Lightweight Battery And Output Thereof

The term "lightweight battery" used herein means batteries light enough that they will not cause the iontophoresis device to release from the skin. Generally speaking, batteries having a weight of 20 g or less, preferably 5 g or less, down to, for example, 0.2 g, are used in the present invention.

The batteries usable in the present invention can be in any form. For example, so-called button batteries, coin batteries, sheet batteries, paper batteries, bar batteries, and so-called microbatteries can be used. Button batteries and sheet batteries can be desirably used for the reasons that they are small or flexible.

The current values required for the iontophoresis are generally 600 $\mu A/cm^2$ or less. Accordingly, since the contact resistance between the electrodes and the skin is several kiloohms to several dozen kiloohms, the output of the battery is generally about 0.5 V to 10 V, although it depends on the applying times, and also on the contact area between the electrodes and the patient's skin. If necessary, two or more batteries can be arranged or laminated to each other in the present iontophoresis device. In addition, a constant current element and a luminescent element for indicating the current flow can be mounted in the iontophoresis device, if desired. For instance, known constant current circuits containing transistors and resistors can be formed as a small and compact chip and can be mounted on, for example, a button battery so as to keep the current constant.

Furthermore, any known polarity exchange means for freely exchanging the polarity (i.e., positive and negative poles) of the electrode, depending upon the polarity of the ionic agent or drug, can be mounted in the present iontophoresis device.

The present invention will now be further illustrated by, but is by no means limited to, the following application examples.

EXAMPLE 1

An iontophoresis device as illustrated in FIGS. 1 to 3 was formed. The electrically conductive viscoelastic gel layers had a thickness of 1.5 mm and an area of 48 $cm^2$ and comprised 20% by weight of the polyacryl amide mentioned above, 30% by weight of distilled water, and 40% by weight of glycerine. The gel layer of first electrode further contained 5% by weight of sodium salicylate. The gel layer of second electrode 3 having an area of 56 $cm^2$, further contained 3% by weight of sodium chloride.

Current-distribution conductive member layers 5 and 7 were composed of aluminum foil. The negative poles of two button batteries (Matsushita Electric Ind. Co., Ltd; BR1225, Li/(CF)n; 0.85 g) 8, each having an output of 3 V, were directly connected, in series, to first electrode 2. The positive poles were connected to second electrode 3. The entire assembly was then integrally laminated with polyethylene film 10 by means of a heat sealing method to form an iontophoresis device. The skin contact impedance of the resultant iontophoresis device was several kiloohms.

The iontophoresis device thus prepared was applied to the patient's skin for 2 hours. The injected amount of the salicylic acid anion was about 8 mg (i.e., about 40% of the theoretical amount). This amount was about 3 to 10 times that of the so-called ordinary cataplasm containing methyl salicilate as a main constituent.

The iontophoresis device of this example can be used as an analgesic and antiphlogistic agent. However, since the so-called galvanization effecting vasodilative function is also conducted, it should be noted that this iontophoresis device exhibits remarkable synergestic effects on disorders such as neuralgia, arthralgia, and rheumatoid arthralgia. The present iontophoresis device can also be used for curing various skin disorders and for injecting various cosmetic skin nutrients including various skin vitamins.

The present iontophoresis device having a first electrode separated from a second electrode as shown in FIG. 6 can be desirably used for curing skin disorders such as trichophytosis on the sole of the foot.

EXAMPLE 2

This example illustrate the application of an iontophoresis device as shown in FIGS. 1 to 3. Conductive gel layers 4 and 6 having the following compositions (% by weight) were used.

|  | Gel layer 4 | Gel layer 6 |
|---|---|---|
| Glycerine | 50 | 60 (containing 2% NaCl) |
| Karaya gum | 45 | 40 |
| Water | 5 | 5 (saturated with NaCl) |

The thickness of gel layers 4 and 6 were 1.5 mm and the areas of gel layers 4 and 6 were 6 $cm^2$ and 12 $cm^2$ respectively.

The current-distribution conductive member layers 3 and 7 were made of carbon containing conductive rubber film. The negative pole of button battery 8 (Matsushita; BR1225) having an output of 3 V was directly connected to first electrode 2 and the positive pole was connected through lead wire 9 to second electrode 3. The entire assembly was then integrally laminated with polyethylene film 10 by means of a heat sealing method to form an iontophoresis device 1.

The iontophoresis device thus prepared was applied to the face skin of patient. Before the application, about 0.2 ml of 10% aqueous solution of sodium ascorbate (stored in an ampule) was dropwise impregnated into conductive gel layer 4 and, then, the iontophoresis device was applied to the affected skin.

The concentration of vitamin C in the skin tissue was about 10 micromol/g after 1 hour application at a current of 50 $\mu A$. This concentration is remarkably higher than the following data reported in Katsu Takenouchi, et al., Vitamines, 28,501 (1963).

|  | micromol/g |
|---|---|
| Normal skin tissue | 0.057 |
| One hour after venoclysis of | 0.400 |

| | micromol/g |
|---|---|
| 5 g of vitamin C Effective concentration for completely inhibiting the formation of melanin (in vitro) | 0.500 |

As is well-known in the art, vitamin C (ascorbic acid) or the derivatives thereof such as sodium ascorbate are effective for curing chromatodermatosis such as the so-called moth patch, freckle, various melanosises. However, as mentioned above, conventional iontophoresis has not been popularized due to the troublesome application although it is known that the iontophoresis is very effective method for curing chromatodermatosis and the like. Contrary to this, the present iontophoresis device can be very effectively and advantageously used for curing various skin disorders and for injecting various cosmetic skin nutrients by very simple operation. This is a dramatical progress in this field.

When this iontophoresis device was applied to the face, vitamin C (i.e. ascorbic acid anion) was injected into the epidermal tissue and the upper layer of the true skin in an extremely high concentration of about 10 or more $\mu$mol/g tissue for 1 or 2 hours application at about 10 to 30 $\mu$A/cm$^2$. The above-mentioned concentration was retained in the tissue for a long time and effecting to inhibit melanin formations in melanocytes.

The invention has been described in detail with particular reference to certain preferred embodiments thereof, but it will be understood that variations and modifications can be effected within the spirit and scope of the invention.

We claim:

1. An iontophoresis device comprising:
   (a) a flexible, non-conductive backing layer;
   (b) first and second conductive electrodes each fixed, in spaced apart relationship, to a part of one side of said flexible backing layer, and each consisting essentially of a flexible current conductive layer fixed on one side to the backing layer and a flexible and electrically conductive gel layer made from a hydrophilic softened or plasticized polymeric substance for containing an ionic agent laminated to the other side of the conductive layer, and
   (c) a lightweight battery, said battery being located between the conductive layer of one of said electrodes and the backing layer so that one of the poles of the battery contacts the conductive layer of said one electrode and a flexible lead wire connecting the other pole of the battery to the conductive layer of the other electrode.

2. The device of claim 1, wherein the conductive layers are flexible, metallic foil.

3. The device of claim 2, wherein the foil is aluminum foil.

4. The device of claim 1, wherein the flexible backing layer is a sheet of polyethylene.

5. The device of claim 1, wherein the gel layers of both electrodes have an adhesive outer surface for attachment of the device to the body.

6. The device of claim 1, wherein the conductive electrodes are located side-by-side on the backing layer with a small gap between, said electrodes covering substantially the entire surface of said one side of the backing layer.

7. The device of claim 1, wherein one conductive electrode concentrically surrounds the other on the backing layer with a gap between them said electrodes together covering substantially the entire surface of said one side of the backing layer.

8. The device of claim 1, wherein the gel layers of the electrodes have an adhesive inner surface for laminating them to their respective conductive layers thereby permitting them to be removed and replaced with new gel layers containing a fresh supply of the ionic agent.

9. The device of claim 1, wherein the polymeric substance of the gel layers is selected from the group consisting of natural resinous polysaccharides, vinyl resins, and acrylic resins.

10. The device of claim 9, wherein said polysaccharides are karaya gum, tragacanth gum, and Xanthan gum.

11. The device of claim 9, wherein said vinyl resins are partially saponified polyvinyl alcohol, polyvinyl formal, polyvinyl methyl ether and copolymers thereof, polyvinyl pyrrolidone, and polyvinyl methacrylate.

12. The device of claim 9, wherein said acrylic resins are polyacrylic acid and sodium salts thereof, polyacrylamide and partially hydrolyzed products thereof, partially saponified products of polyacrylic acid esters, and copolymers of acrylic acid and acrylamide.

* * * * *